United States Patent [19]
Giacobbe et al.

[11] Patent Number: 5,417,869
[45] Date of Patent: May 23, 1995

[54] SURFACTANTS AND CUTTING OIL FORMULATIONS USING THESE SURFACTANTS WHICH RESIST MICROBIAL DEGRADATION

[75] Inventors: Thomas J. Giacobbe, Skillman, N.J.; Frederick C. Loveless, Yardley, Pa.; Carl R. Mackerer, Pennington, N.J.; Norman J. Novick, Holland; Douglas G. Placek, Bensalem, both of Pa.

[73] Assignee: Mobil Oil Corporation, Fairfax, Va.

[21] Appl. No.: 179,998

[22] Filed: Jan. 10, 1994

Related U.S. Application Data

[63] Continuation of Ser. No. 8,853, Jan. 25, 1993, abandoned, which is a continuation of Ser. No. 441,795, Nov. 27, 1989, abandoned.

[51] Int. Cl.⁶ .................. C10M 169/04; C10M 173/00
[52] U.S. Cl. .................. 252/33.6; 252/34.7; 252/49.5; 252/49.8; 252/52 R
[58] Field of Search ............ 252/336, 49.5, 56 R, 252/17, 32, 34, 38, 39, 40, 107, 108, 34.7, 49.8, 52 R

[56] References Cited

U.S. PATENT DOCUMENTS

| | | | |
|---|---|---|---|
| 2,717,266 | 9/1955 | Lemieux | 260/530 |
| 2,997,447 | 8/1961 | Russell et al. | 252/107 |
| 2,999,064 | 9/1961 | Sluhan | 252/34.7 |
| 3,284,363 | 11/1966 | Bright | 252/107 |
| 3,392,117 | 7/1968 | Glasson | 252/17 |
| 3,607,761 | 9/1971 | Feighner et al. | 252/108 |
| 3,791,970 | 2/1974 | Tubb | 252/12 |
| 3,879,309 | 4/1975 | Gatti et al. | 252/117 |
| 3,925,414 | 12/1975 | Landis et al. | 260/327 R |
| 4,022,713 | 5/1977 | Waldstein | 252/34 |
| 4,071,675 | 1/1978 | Yu et al. | 526/193 |
| 4,093,581 | 5/1978 | Anderson | 260/29.6 |
| 4,228,304 | 10/1980 | Noda et al. | 562/507 |
| 4,442,018 | 4/1984 | Rand | 252/307 |
| 4,759,861 | 7/1988 | Ogura et al. | 252/41 |
| 4,839,080 | 6/1989 | Jungermann et al. | 252/107 |
| 4,853,140 | 8/1989 | Payne et al. | 252/34 |
| 4,859,352 | 8/1989 | Waynick | 252/41 |

FOREIGN PATENT DOCUMENTS 2007229 9/1970 Germany.

Primary Examiner—Margaret Medley
Attorney, Agent, or Firm—Alexander J. McKillop; Malcolm D. Keen; Jessica M. Sinnott

[57] ABSTRACT

The invention relates to bioresistant surfactants and cutting fluid compositions which utilize them. The surfactants consist of soaps of carboxylic acid compounds having from 10 to 30 carbon atoms, the carbon skeleton of which is branched and not straight chain. It is the branching which lends the resistance to biodegradation to the products of the invention. Further enhanced bioresistance may be obtained by utilizing a branched lubricating basestock material in the cutting fluid composition.

8 Claims, 1 Drawing Sheet

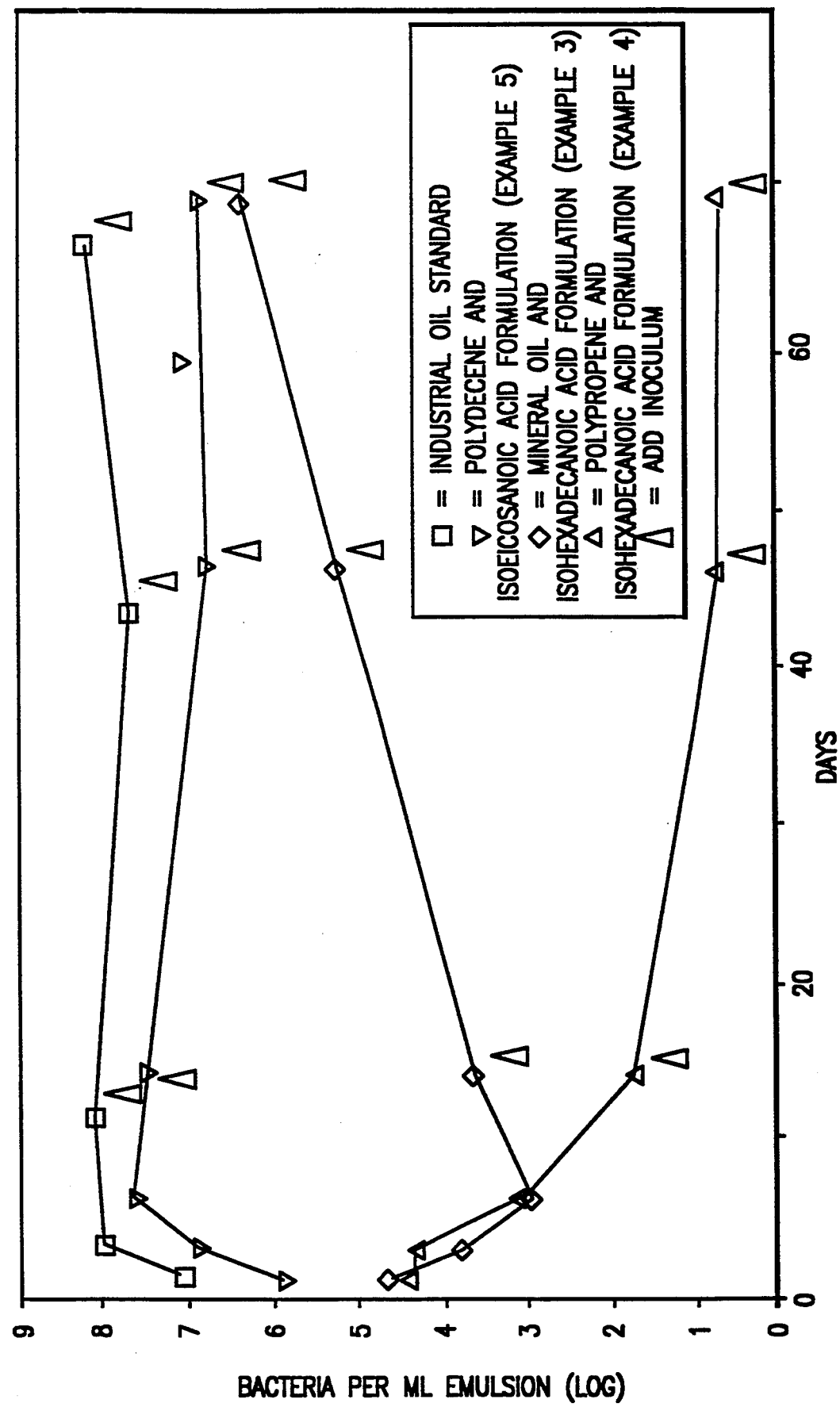

SURFACTANTS AND CUTTING OIL FORMULATIONS USING THESE SURFACTANTS WHICH RESIST MICROBIAL DEGRADATION

This is a continuation of application Ser. No. 08/008,853, filed on Jan. 25, 1993, now abandoned which is a continuation of application Ser. No. 07/441,795, filed on Nov. 27, 1989, now abandoned.

BACKGROUND OF THE INVENTION

1. FIELD OF THE INVENTION

This invention relates to a new class of bioresistant surfactants and their use in formulating cutting fluids providing excellent corrosion inhibition, lubrication and most significantly, resistance to microbial degradation.

2. DESCRIPTION OF THE PRIOR ART

Modern metal working and forming processes normally require the use of cutting fluids whose function is to facilitate the machining operations by (1) cooling and (2) lubricating. The cooling function is accomplished by the ability of the fluid to carry off the heat generated by the frictional contact between the tool and the workpiece and/or any heat resulting from the plastic deformation of the work. Cooling aids tool life, preserves tool hardness and helps to maintain the dimensions of the machined parts. The second function is accomplished by the ability of the fluid to lubricate the tool-workpiece interface in order to reduce tool wear, frictional heat generation and power consumption. The presence of a fluid also serves to carry away debris from the work area.

In addition to the primary functions of cooling and lubricating, cutting fluids should protect the machined surfaces, tools and other equipment from rust and corrosion; should not themselves corrode, discolor or form deposits in or on the work area, and should not produce undesirable fumes or smoke. And, in those instances where skin contact is unavoidable, the cutting fluid compositions should be non-toxic and dermatologically safe.

Moreover, the cutting fluid composition itself should, ideally, have some stability against microorganisms. Bacteria and fungi frequently spoil soluble cutting fluids (especially oil in water emulsions) during machining operations. Not surprisingly, the cutting environment, which contains warm water and an available carbon source, provides a good medium for microorganism growth. Spoilage often manifests itself first as a foul smell. Furthermore, spoilage can cause color change, emulsion break, acidity increase, and sludge formation. Any of these signal a need to change the cutting fluid. Under severe conditions of use, changes due to biological fouling can be required every few days.

To remedy this situation, it is conventional in the art to add various "biocides" to cutting fluid compositions in order to control microbial growth and thus extend fluid life. However, biocides present their own problems. Some cause contact dermatitis, and others cause allergic dermatitis. Still others, through in situ modification, become suspect carcinogens. Government regulations and worker concern about biocide exposure further inhibit their use. Even in situations where the added biocides have no known adverse reaction to humans, biological fouling of the cutting fluid can still occur within a short time and lead to the serious problems of offensive odor, filter plugging, eventual loss of lubricative properties and corrosion of parts and machinery caused by acidic by-products generated by the microorganisms. Furthermore, if the cutting fluid is employed in the form of a stable emulsion with water, biological fouling can lead to the breaking of the emulsion. An ideal cutting fluid would thus contain no biocide while exhibiting bioresistance for prolonged periods of use.

Various types of cutting fluids are known in the art which embody certain of the desired characteristics delineated above. However, they also lack one or more of the same, such as corrosion resistance, biocidal activity and/or drill life performance, to the extent that they are inadequate in meeting the demands of practical industrial applications. Water, for example, is one of the most effective coolants available but can seldom be used as an effective cutting fluid in that it has little value as a lubricant and further it will promote rusting of ferrous work pieces. One method of combining the cooling properties of water with the lubricating properties of oil is through the use of soluble oils. These soluble oils are compounded so they will be able to form a stable emulsion with water. In such cases, the main component of the emulsion, i.e. water, provides effective cooling while the oil and other compounds impart the desirable properties of lubrication and corrosion resistance. Still, these emulsions often fall short of possessing all of the above-mentioned qualities required in a cutting fluid and, as such, remain somewhat inadequate for the rigors of practical metal working and machining operations.

As an example, U.S. Pat. No. 2,999,064 discloses a stable aqueous cutting fluid comprised of a mixture of boric acid, unsaturated fatty acids, such as those derived from oleic acid, and alkanolamines. While aqueous solutions are used as cutting fluids, their anti-corrosive character is found to be inadequate for practical use and they have the added disadvantage of foaming. Most importantly, the essential compounds of these cutting fluids do not themselves possess adequate bioresistance, hence requiring the use of exogenous biocidal compounds, which, of course, suffer from the drawbacks mentioned previously.

In DE-OS 1620447 and DE-OS 2007229, salts or condensation products of alkanolamines and orthoboric acid are described as being foamless, water-hardening nonreactive rust inhibitors with fungistatic and bacteriostatic action. However, the corrosion inhibiting action of these compositions has also proven to be inadequate in actual practice.

U.S. Pat. No. 4,022,713 describes the reaction product of orthoboric acid and monoalkanolamines having one to three carbon atoms in the alkanol chain. These compounds possess bactericidal and fungicidal properties; however, they must be added separately to the cutting fluid composition for this purpose and, in any event, they manifest the inadequacies attendant exogenous biocides.

Lastly, soluble cutting oils, such as those exemplified by the current industrial standards, are known to degrade biologically, suggesting that oleic acid or other fatty acids, acting as a surfactant in these fluids, contributes most to spoilage by supplying food for microbial growth. As surfactants, sulfonates can replace carboxylates. However, sulfate-reducing bacteria convert sulfonates to hydrogen sulfide, a well known malodorant. In addition, the typical cutting fluid basestock—namely, mineral oil, contains normal paraffins which can also provide food to microorganisms.

Thus it has been discovered that highly branched surfactants when formulated into a cutting oil, resist microbial degradation without resort to externally added biocides while at the same time meeting all commercial standards of performance. Further, formulation of the cutting fluid using a branched basestock is found to enhance the bioresistance of the final fluid or emulsion.

SUMMARY OF THE INVENTION

The present invention is directed to a new class of cutting fluid compositions which overcome the inadequacies of fluids currently used in the art. The compositions of the invention are, in part, soluble cutting oils which when formed into stable emulsions provide a cutting fluid having excellent properties of metal-to-metal lubrication and corrosion inhibition. In drill-life performance tests, the cutting oils of the invention matched fluids recognized as being standards in the industry. Further, the compositions of the invention outperformed these fluids in maintaining their color, and in not developing objectionable odor, sticky residues or sump deposits.

Most significantly, however, the products of the invention are biologically stable and surprisingly do not require the use of an added biocide. This unique stability is achieved through the use of a novel surfactant which itself has the ability to resist microbial degradation due to its particular structure. It has thus been discovered that the soap form of a branched chain carboxylic acid compound having from 10 to 30 carbon atoms is resistant to the biodegradation associated with known cutting fluids. This resistance obviates the need for exogenous biocides, thus eliminating the drawbacks attendant their use.

In accordance therewith the present invention is directed to a bioresistant surfactant which comprises a soap derived from a carboxylic acid compound having from 10 to 30 carbon atoms of the formula:

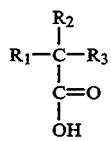

wherein $R_1$ is hydrogen or an alkyl group; $R_2$ is hydrogen or an alkyl group; and $R_3$ is an alkyl group, provided that the number of carbon atoms of $R_1$ plus $R_2$ plus $R_3$ is from 8 to 28 and that when $R_1$ and $R_2$ are hydrogen, the $R_3$ alkyl group has a non-linear, i.e., branched, carbon skeleton. When only $R_1$ is hydrogen, the $R_2$ and $R_3$ alkyl groups may each have straight chain carbon skeletons because the branching necessary to obtain bioresistance is provided by the bonds from the alpha-carbon to the $R_2$ and $R_3$ alkyl groups, these bonds forming a "Y" branch. While this configuration will afford bioresistance to the molecule, if increased bioresistance is desired, then either or both of these $R_2$ and $R_3$ alkyl groups may themselves be branched, that is, have a non-linear carbon skeleton. In general, the greater the branching on any or all of the alkyl groups, $R_1$, $R_2$ and/or $R_3$, the greater the resistance of the molecule to microbial degradation.

The invention is further directed to the use of this surfactant in formulating a bioresistant cutting fluid composition further containing a lubricative basestock material. The lubricative basestock material may also have a branched carbon skeleton, the branching being sufficient to provide bioresistance to the basestock material thus enhancing the bioresistance of the cutting fluid composition. Other known additives may be incorporated into the cutting fluid formulation depending upon particular requirements.

BRIEF DESCRIPTION OF THE DRAWING

FIG. 1 graphically depicts bacterial growth as it occurs in various cutting oil emulsions over time. Included among the cutting oil emulsions represented in FIG. 1 is a known industrial standard and cutting formulations of the present invention, exemplified by the amine soap surfactant of isoeicosanoic acid using polydecene as basestock, and the amine soap surfactant of isohexadecanoic acid using mineral oil and polypropene, respectively, as basestocks. The data are plotted as bacteria per milliliter of emulsion versus time as measured in days.

DETAILED DESCRIPTION OF THE INVENTION

The products of the present invention incorporate the requirements needed in a practical cutting fluid. Namely, the products of the present invention are themselves resistant to microbial degradation, provide excellent corrosion inhibition, lubrication, are non-toxic and dermatologically safe.

The cutting fluid products of the present invention are prepared using the bioresistant surfactants of the invention. Generally, these surfactants are soaps derived from highly branched carboxylic acid compounds which have from 10 to 30 carbon atoms in total. Any soap form of these carboxylic acids which does not form a precipitate is useful in the invention. Preferred soaps include those formed from amines, alkali metals, such as sodium or potassium, or alkaline earth metals so long as they are soluble in the cutting oil concentrate formulation and in the final emulsion. Branching, a non-linear carbon skeleton of the carboxylic acid, renders these surfactants bioresistant. The term bioresistant refers, of course, to an ability to withstand degradation by various microorganisms.

These non-straight chain, or branched carboxylic acids are preferably saturated aliphatic compounds, such as, for example, isohexadecanoic acid or isoeicosanoic acid. Isohexadecanoic acid and isoeicosanoic acid, compounds useful in the practice of the invention, have been prepared from Guerbet alcohols. Guerbet alcohols, sometimes called dimer alcohols, have two pertinent features; each contributes toward making bioresistant surfactants. First, they are primary alcohols. As such, oxidation converts them to carboxylic acids. Neutralization transforms these to soaps.

Second, Guerbet alcohols have a "Y" branched carbon skeleton. This branch arises during the Guerbet reaction, a base-catalyst dimerization of two alcohols. This branching hinders microbial degradation. Also, depending on the starting alcohol for the Guerbet reaction, each leg of the "Y" branch can itself have multiple branches which further slow biodegradation. Two commercially available dimerized methyl-branched alcohols, having a total of sixteen and twenty carbon atoms, respectively, (also known as $C_{16}$ and $C_{20}$ Guerbet alcohols), were chosen to demonstrate, without limiting, the practice of the present invention.

To provide the corresponding $C_{16}$ and $C_{20}$ carboxylic acids, potassium permanganate oxidation of isohexadecanol (the $C_{16}$ Guerbet alcohol) and isoeicosanol (the $C_{20}$ Guerbet alcohol) was performed. The details of the oxidation reaction are set forth in Example 1 and Example 2. The scheme of the oxidation reaction was as follows:

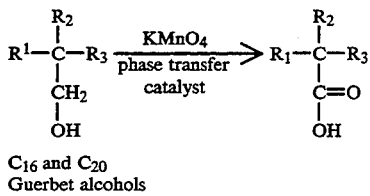

$C_{16}$ and $C_{20}$ Guerbet alcohols

For one skilled in the art, various methods provide the same or similar acids. Some of these methods include olefin carboxylation or carbonylation followed by oxidation. Also, aldol condensation followed by oxidation and hydrogenation will provide these acids.

Amine soaps of these fatty acids were utilized in the formulations of the present invention; the amine soaps being formed, for example, by reaction with the alkanolamine components, such as triethanolamine, upon blending of the ingredients to form the soluble cutting oil. The soaps can, of course, be formed by separate reactions well known in the art and need not depend upon the blending of any particular ingredients.

Generically, $R_1$ and $R_2$ may both be hydrogen and if so, $R_3$ is a branched alkyl group having anywhere from 8 to 28 carbon atoms, which when added to the carbon atoms of the carboxylic functional group and the alpha-carbon, i.e. the carbon bearing the carboxyl group, brings the total number of carbons to a total of 10 to 30. In this particular case, where $R_1$ and $R_2$ are both hydrogen, it is the branching of the $R_3$ group that affords bioresistance to the molecule. Preferably, this branching consists of a methyl group located at every second carbon atom of the $R_3$ alkyl group. As the frequency of branching decreases, so does bioresistance.

In the situation where only $R_1$ is hydrogen, and $R_2$ and $R_3$ are alkyl groups, the $R_2$ and $R_3$ alkyl groups need not have branched carbon skeletons. The branching, necessary to afford the bioresistant properties to the molecule, is provided by the bonds from the alpha-carbon to $R_2$ and $R_3$; the bonds forming a "Y" branch with $R_2$ and $R_3$ the legs of the branch.

Similarly, in the case where $R_1$ is also an alkyl group, i.e., all three substituent groups $R_1$, $R_2$, and $R_3$ are alkyl, $R_1$ need not be branched as the bond from the alpha carbon to $R_1$ forms an additional leg, or branch over and above that provided by $R_2$ and $R_3$.

In all cases, bioresistance may be increased by increasing the branching on the $R_1$, $R_2$, and/or $R_3$ alkyl groups. In general, more methyl branches give greater bioresistance. Thus, a molecule having methyl group on every B0 second carbon atom of the $R_1$, $R_2$ and/or $R_3$ alkyl groups will be very bioresistant. As the frequency of this alkyl group branching decreases, so does the resistance of the molecule to microbial degradation.

The following examples illustrate, without limiting the present invention.

EXAMPLES

EXAMPLE 1

This example illustrates the preparation of isohexadecanoic acid. Isohexadecyl alcohol, a dimer or Guerbet alcohol which is commercially available, was utilized as a starting material. Following a known oxidation procedure, such as that described in "Oxidation in Organic Chemistry", Part D, W. S. Trahanovsky, Ed.; Academic Press, New York (1982) pp. 193-6, using potassium permanganate and phase transfer conditions with methyltrialkyl ($C_8$-$C_{10}$) ammonium chloride and dichloromethane as solvent, isohexadecanoic acid was formed. The isohexadecanoic acid, an amber liquid, had an acid number of 196.5 (mg KOH/100g, ASTM D-974) and viscosity of 63 cSt at 40° C. The infrared spectrum showed O-H stretch (3400-2400 cm$^{-1}$), and carbonyl stretch of a carboxyl group (1707 cm$^{-1}$).

EXAMPLE 2

This example illustrates the preparation of isoeicosanoic acid. Isoeicosanol, a dimer or Guerbet alcohol which is commercially available was utilized as a starting material and was oxidized to isoeicosanoic acid using the same oxidation procedure as delineated in Example 1. The isoeicosanoic acid, an amber liquid, had an acid number of 163 (mg KOH/100g; ASTM D-974) and viscosity of 91 cSt at 40° C. The infrared spectrum showed O-H stretch (3400-2400 cm$^{-1}$), and carbonyl stretch of carboxyl group (1707 cm$^{-1}$).

These oxidation reactions may, of course, be utilized in forming carboxylic acids from other branched, or non-straight chain, alcohols or aldehydes which would have utility in preparing the surfactants of the present invention. The soap form of these carboxylic acid compounds is that which is useful as a surfactant in the present invention.

Preferably, these carboxylic acid compounds are present in the form of an amine soap, an alkali metal soap or an alkaline earth metal soap so long as solubility in the cutting oil concentrate and in the final emulsion is maintained; that is, any of these materials may be used to form the soap so long as no precipitates are formed. The amine soap is formed, for example, by reaction of the carboxylic acids with an alkanolamine, such as triethanolamine. This alkanolamine may constitute an additive in forming the actual cutting fluid composition, thus forming the soap in situ and conveniently eliminating the need for separate reactions.

The bioresistant cutting fluid compositions of the present invention are most essentially comprised of the surfactant of the invention and a lubricating basestock material, such as mineral oil, which of course is the industry standard and serves well as a benchmark in evaluating various cutting fluids. While mineral oil (for example, solvent refined neutral paraffinic oil) may be used in the practice of the invention it is preferred to use synthetic oils, such as for example polydecene, which recent environmental studies have shown as degrading biologically more slowly than mineral oil. This slower degradation, of course, translates into even greater cutting oil stability.

Most preferably, the lubricative basestocks used in formulating the cutting fluid are comprised of components which themselves are branched, i.e. have a carbon skeleton profile which is not straight chain, much like that of the surfactants of the invention. This branching lends further bioresistance to the final product, thus enhancing the useful life even more. An example of a basestock having a highly branched carbon profile is polypropene, which, in theory, contains a methyl group on every second carbon in the backbone. Other lubricative basestocks, useful in the present invention, having the preferred branched skeleton include copolymers of propylene and butene; polybutene, polyisobutylene; and liquid ethylene-propylene copolymer. Hydrogenated liquid polybutadiene and polyisoprene are also preferred provided they possess the proper microstructure; that is, that they are polymerized in other than a head-to-tail fashion so as to provide a branched polymer structure. Any other alpha-olefins may be effectively utilized as a basestock material especially if the carbon profile is branched. This branched structure favorably affects the biodegration resistance of the formed fluid without affecting the necessary lubricating qualities.

Other known additives may, as a practical matter, be incorporated into the bioresistant cutting fluid composition of the present invention. These may be added, for example, to enhance properties already present in the fluid composition or to provide properties not present in the base stock. Functionally, such additives may lend increased extreme-pressure activity to the fluid; increase corrosion inhibition; metal cleaning; friction reduction of the fluid; or may further provide defoamant or biostatic properties to the fluid. Specifically, these additives generally include an organo-phosphate ester, such as an alcohol ethoxyphosphate which is, for example, a fatty alcohol of approximately 5 to 6 mol ethylene oxide esterified to mono- and diesters of phosphoric acid; an alkanolamine, such as triethanolamine; a boric acid ester of an alkanolamine, such as boric acid ester of mono- and tri-ethanolamine; and an acetylenic diol, such as 2,4,7,9-tetramethyl-5-decyne-4,7-diol. Various esters, which increase lubricity, may optionally be used in the formulation.

Besides being a surfactant, phosphorus from the alcohol ethoxyphosphate contributes extreme pressure activity. The borate ester inhibits microorganism growth in addition to its anti-rust and extreme-pressure activity. Table 1 lists without limiting, the various components which may be used to formulate a practical bioresistant cutting fluid composition in accord with the invention. The functionality and commercial source of these components are also listed.

TABLE 1

Cutting oil components, their source, and function(s)

| COMPONENTS | SOURCE | FUNCTION(S) |
| --- | --- | --- |
| Basestocks | | |
| Mineral Oil | Mobil Oil Corporation | lubricant |
| polydecene (PAO) | Mobil Oil Corporation | lubricant |
| polypropene | Amoco Petroleum Additives Company | lubricant |
| Additives | | |
| isohexadecanoic acid | See Example 1 | surfactant |
| isoeicosanoic acid | See Example 2 | surfactant |
| alcohol ethoxyphosphate | GAF Corporation | surfactant and extreme pressure (EP) activity |
| reaction product of mono- and tri-ethanolamine and boric acid | Climax Performance Materials | rust preventer metal cleaner, extreme pressure activity and biostat activity |
| 2,4,7,9-tetramethyl-5-decyne-4, 7-diol | Air Products | surfactant and defoamant |
| esters of oxidized petroleum hydrocarbons | Alox Corporation | friction-reducer |

Using these components, or purposes of exemplification, five cutting oil concentrates were blended. Each used a different combination of surfactant and basestock. For example, using isohexadecanoic acid in its amine soap form (which reaction occurs with the alkanolamine component during the formulation of the fluid composition) as the bioresistant surfactant, three cutting oil concentrates were prepared using mineral oil, polypropene and polydecene, respectively, as basestocks. See Examples 3, 4, and 6. Two other cutting oil concentrates were prepared using isoeicosanoic acid as the underlying structure of the surfactant, with polydecene and polypropene separately as basestocks; see Examples 5 and 7.

The bioresistant cutting fluid compositions of Examples 3-7 are in what is commonly considered to be concentrated form. When used for their end purpose these concentrates are normally mixed with water so as to produce emulsions, as illustrated in Example 8.,

EXAMPLE 3

This example illustrates the preparation of a soluble cutting oil concentrate formulation using isohexadecanoic acid as surfactant and mineral oil as basestock. The following ingredients were blended sequentially while warming to about 50° C.

| Ingredient | Commercial Source | Parts, by Weight |
| --- | --- | --- |
| (1) Solvent refined neutral paraffric oil | Mobil; Stk 141 | 35 |
| (2) Alcohol ethoxy-phosphate ester | GAF; Gafac RD-510 | 12 |
| (3) Triethanol amine | | 10 |
| (4) Isohexadecanoic acid | See Example 1, above | 31 |
| (5) Boric acid ester of triethanol amine | Climax Performance Materials, Atracor-T | 10 |
| (6) Acetylenic diol | Air Products, Surfynol 104BC | 1 |
| (7) Oxidized hydro-carbon ester | Alox Corp, Alox 350 | 1 |

EXAMPLE 4

This example illustrates the preparation of a soluble cutting oil concentrate formulation using isohexadecanoic acid as surfactant and polypropene oil as basestock. The following ingredients were blended sequentially while warming to about 50° C.

| Ingredient | Commercial Source | Parts, by Weight |
| --- | --- | --- |
| (1) Polypropene | Amoco; A-9011 | 47 |
| (2) Alcohol ethyoxy phosphate ester | GAF; Gafac RD-510 | 10 |
| (3) Triethanol amine | | 6 |
| (4) Isohexadecanoic acid | See Example 1, above | 25 |
| (5) Boric acid ester of triethanol amine | Climax Performance Materials, Atracor-T | 10 |
| (6) Acetylenic diol | Air Products Surfynol 104BC | 1 |
| (7) Oxidized hydro-carbon ester | Alox Corp; Alox 350 | 1 |

EXAMPLE 5

This example illustrates the preparation of a soluble cutting oil concentrate formulation using isoeicosanoic acid as surfactant and polydecene (PAO) as basestock. The following ingredients were blended sequentially while warming to about 50° C.

| Ingredient | Commercial Source | Parts, by Weight |
|---|---|---|
| (1) Polydecene | Mobil; Stk 509 | 40 |
| (2) Alcohol ethoxy phosphate ester | GAF; Gafac RD-510 | 12 |
| (3) Triethanol amine | | 7 |
| (4) Isoeicosanoic acid | See Example 2, above | 30 |
| (5) Boric acid ester of triethanol amine | Climax Performance Materials, Atracor-T | 10 |
| (6) Acetylenic diol | Air Products Surfonyl 104BC | 1 |

EXAMPLE 6

This example illustrates the preparation of a soluble cutting oil concentrate formulation using isohexadecanoic acid as surfactant and polydecene oil as a basestock. The ingredients listed below were blended sequentially while warming to about 50° C.

| Ingredient | Commercial Source | Parts, by Weight |
|---|---|---|
| (1) Polydecene | Mobil; Stk 509 | 53 |
| (2) Alcohol ethoxy phosphate ester | GAF; Cafac RD-510 | 10 |
| (3) Triethanol amine | | 6 |
| (4) Isohexadecanoic acid | See Example 1, above | 20 |
| (5) Boric acid ester of triethanol amine | Climax Performance Materials, Atracor-T | 10 |
| (6) Acetylenic diol | Air Products Surfonyl 104BC | 1 |

EXAMPLE 7

This example illustrates the preparation of a soluble cutting oil concentrate formulation using isoeicosanoic acid as surfactant and polypropene oil as basestock. The ingredients listed below were blended sequentially while warming to about 50° C.

| Ingredient | Commercial Source | Parts, by Weight |
|---|---|---|
| (1) Polypropene | Amoco; A-9011 | 33 |
| (2) alcohol ethoxy phosphate ester | GAF; Gafac RD-510 | 12 |
| (3) Triethanol amine | | 7 |
| (4) Isoeicosanoic acid | See Example 2, above | 30 |
| (5) Boric acid ester of triethanol amine | Climax Performance Materials, Atracor-T | 20 |
| (6) Acetylenic diol | Air Products, Surfonyl 104BC | 1 |

EXAMPLE 8

This example illustrates the preparation of cutting oil emulsions from the cutting oil concentrate formulations. The five formulations of Examples 3–7 were all yellow liquids, and quickly bloomed into stable emulsions when added to lightly stirred water at a volume ratio of concentrate to water of 6:100. The amount of water used in forming stable emulsions with the novel cutting fluid compositions depends upon the particular cutting or metal working operation in which the fluid is to be employed; the amount of dilution required for a specific application being readily determined from conventional experience. For example, when drilling operations are performed, lubrication becomes important hence requiring a slightly more concentrated emulsion. Normally, for drilling, the preferred volume ratio of concentrate to water is about 6:100. On the other hand, when grinding operations are performed, the cooling of the work piece becomes important, more so than lubrication, hence a slightly more dilute emulsion may be used. Here a preferred volume ratio of concentrate to water would be about 0.5:100 or about 1:100. In general, the low end of emulsion concentration ratio for practical purposes is about 0.5:100. The upper end, of course, depends on economics and not functionality. Thus in theory, the cutting oils of the present invention could be used in their concentrate form; however, in terms of cost efficiency, the upper limit of volume ratio of concentrate to water is about 10:100.

The cutting oil concentrate formulations of Examples 3–7, as well as emulsions formed from them, were evaluated under the following criteria with the following results:

(1) free oil (unemulsified concentrate): all cutting oil concentrates, Examples 3–7, emulsified well and each left only a trace of free oil.

(2) stability: each emulsion remained stable more than a month (test duration). An opalescence showed small emulsion particles which likely contribute to the stability.

(3) hard water compatibility: the cutting oil concentrates of Examples 3–5 emulsified in 500 ppm ($CaCO_3$ equivalent) synthetic hard water. No unusual deposits or additive precipitates were observed.

(4) emulsion breaking by acidifying: adding hydrochloric acid, sulfuric acid or magnesium sulfate (an acidic salt) broke the emulsions. After setting 16 hours, the oils and aqueous layers separated easily. The industry commonly uses acid to break emulsions and collect the oil for disposal.

EXAMPLE 9

This example illustrates the biodegradation testing performed with the present invention. In these tests, the bacterial inoculum was a composite of spoiled cutting fluids that came from industrial users across the U.S. Besides an initial heavy dose, smaller periodic inoculations of fresh bacteria challenged various emulsions of the present invention. This simulated field conditions where exogenous bacteria continually contaminate fluids. Standard plate counting techniques gave bacterial concentration of periodic aliquots. Fungal growth was also looked for in each sample.

Procedurally, the method for determining the rate of biological growth in the cutting oil emulsions of the present invention was as follows:

Standard plate counting methods gave changes in microorganism numbers. Different plating media separated microbial populations into two groups, aerobic bacteria and fungi. Initially, 100 ml of the cutting oil emulsion (6 ml of oil concentrate in 100 ml of water) was added to a cotton stoppered 250 ml Erlenmeyer flask. It was inoculated with 0.5 ml of heavily contaminated cutting fluid, and placed on a rotary shaker at 150 rpm and 25° C. At appropriate sampling times, 1 mL of the inoculated formulation was removed from the flask and added to a 25 ml test tube containing 9 ml of sterile water. Further 1:10 dilutions of the cutting fluid were made until 0.1 ml gave 30–300 colonies on a test plate. To insure proper colony count, one dilution above and below the estimated dilution was also plated. All plating used 0.1 mL and standard aseptic techniques. All appropriate dilutions were plated in duplicate. For total aerobic bacterial counts, platings were made onto one-half strength trypticase soy agar (BBL). Fungi were quantified with plating onto potato dextrose agar (Difco) containing 70 ppm Rose Bengal to inhibit bacterial growth. Plates for bacterial counts were incubated at 37° C. for 48 hours before counting colonies. Plates for fungal counts were incubated at 25° C. for 2–5 days before enumeration. Results of a 69 day test using emulsions prepared from the concentrates of Examples 3, 4, and 5 are graphically indicated at FIG. 1 and are tabulated, in part, in Table 2 below.

As illustrated by FIG. 1, the cutting oil formulated from isohexadecanoic acid (in amine soap form) with polypropene as basestock, as in Example 4, proved to be the most bioresistant. The control, an industrial standard without biocide, exhibited the least bioresistance. Cutting oils formulated from isohexadecanoic acid (in its amine soap form) as surfactant and mineral oil as basestock, as in Example 3, and isoeicosanoic acid (in its amine soap form) as surfactant and polydecene as base stock, as in Example 5, fell between these two. After an initial spike, bacteria levels in the polypropene and isohexadecanoic acid emulsion steadily declined. They finally reached about 10 bacteria per milliliter, about 100 million fewer than the industrial standard. None of the emulsions showed overt signs (odor, color change, emulsion break, etc) of spoilage.

These results support the hypothesis that highly branched surfactants resist biodegration by not providing microorganism food. The results also indicate that branched base stock materials enhance this resistance. Though lower than the control, the polydecene (PAO) formulation supported surprisingly high bacterial levels. Presumably, bacteria saw the $C_8$ (and other) pendant chains from the polydecene backbone as normal paraffins which they metabolize. Nevertheless, these levels were still lower than those exhibited by the control industrial standard currently used.

TABLE 2

| EMULSION | TOTAL AEROBIC BACTERIAL COUNT (per ml of emulsion) | | |
|---|---|---|---|
| | 24 hrs | 72 hrs | 144 hrs |
| Example 3, see above | $4.4 \times 10E4$ | $6.5 \times 10E3$ | $1.2 \times 10E3$ |
| Example 4, see above | $2.5 \times 10E4$ | $2.0 \times 10E4$ | $1.4 \times 10E3$ |
| Example 5, see above | $7.6 \times 10E5$ | $7.2 \times 10E6$ | $3.9 \times 10E7$ |
| Industrial Standard (without biocide) | $1.2 \times 10E7$ | $1.0 \times 10E8$ | — |

No fungi were observed during this test. All samples had bacterial counts below that of the industrial standard without its biocide.

EXAMPLE 10

This example illustrates a lubrication performance test. A six percent emulsion of the present invention was added to the cup of a Four-Ball Wear Testing apparatus along with 4 new balls. This test procedure is a modification of ASTM Test D2266. The general procedure for this test is as follows: three steel balls are held in a ball cup. A fourth ball positioned on a rotatable vertical axis is brought into contact with the three balls and is rotated against them. The force with which the fourth ball is held against the three stationary balls may be varied according to a desired load. Test emulsions of the present invention (in 6:100 ratios) were added to the ball cup and acted as lubricants for the rotation. At the end of the test, the steel balls were investigated for wear-scar; the extent of scarring representing the effectiveness of the test emulsion as an antiwear agent. In the lubrication performance testing of the various six-percent emulsions of the instant invention, the Four-Ball Wear Testing apparatus was heated to 40° C., and rotated at 1800 rpm with a 40 kg load for 1 hour. The scar diameter on each of the 3 stationary balls was measured, and an average calculated. The results obtained are shown in Table 3 below.

Test runs 1–4 show comparative results using conventional lubricants.

TABLE 3

| TEST | MATERIAL | SCAR DIAMETER, mm |
|---|---|---|
| 1 | Industrial Standard #1 | 0.9, 0.83 |
| 2 | Industrial Standard #2 | 1.1, 1.0 |
| 3 | Industrial Standard #3 | 0.82 |
| 4 | Industrial Standard #4 | 0.77 |
| 5 | Example 3, see above | 0.74 |
| 6 | Example 4, see above | 0.68 |
| 7 | Example 5, see above | 0.67 |

As evidenced by this data, the cutting oil formulations of the present invention resulted, on the average, in less wear-scarring than did the conventional lubricants.

EXAMPLE 11

This example illustrates a malleable iron rusting test using emulsions formed from the present invention. Two grams of malleable iron chips were placed in a beaker and swirled for 0.5 min with one of the six percent emulsions of the present invention. The emulsion used was then drained off the chips, and the moistened chips were separated from each other. The beaker was covered with a watch glass to retain residual moisture, and the chips were periodically observed over 24 hours. The results obtained are shown in Table 4 below.

TABLE 4

| TEST | EMULSION | OBSERVATION |
|---|---|---|
| 1 | From Example 3 | No rust after 24 hr. |
| 2 | From Example 4 | No rust after 24 hr. |
| 3 | From Example 6 | No rust after 24 hr. |
| 4 | Water (control) | First rust seen in 3 hr; heavy rust in 24 hr. |

EXAMPLE 12

This example illustrates drill-life performance tests utilizing the formulations of the present invention. In drill-life tests, the cutting oil formulations of Examples 3, 4, 5 in emulsion form (6:100) were found to perform as well as two widely-known commercial standards. During the drill-life test, the cutting fluid continually flooded the work piece. Each fluid was tested twice at each of the three cutting speeds: 75, 100, and 150 feet per minute. Small differences existed, but no fluid was consistently better (or worse) at all speeds. No significant difference in performance among the five fluids was found. Surprisingly, and not fully explainable, the two commercial standards gave similar but not superior drill-life performances. One of the commercial standards, as a heavy duty oil, contains sulfurized fat and chlorinated wax which should improve performance. Table 5 below presents the results of the test.

In addition to these drill-life tests, other observations were made. The cutting oils of the invention did not have an objectionable odor and their color, a milky-white, was maintained throughout the test. In contrast, the industrial standard developed a brown tinge which machinists often associate with rust. Further, the cutting oils of the invention did not rust the machinery nor remove its paint. Also, they did not leave a sticky residue nor deposits in the sump.

TABLE 5

MACHINING PARAMETERS AND TEST RESULTS
drill: ¼ inch diameter jobber length
feed: 0.005 inch per revolution
depth of cut: 0.5 inch, blind
drill life end point: 0.015 inch wear

| CUTTING SPEED: ft/min | DRILL LIFE: number of holes | | | | |
|---|---|---|---|---|---|
| | Indus. Stand. #1 | Example 4 | Example 5 | Example 3 | Indus. Stand. #2 |
| 150 | 15 | 15 | 25 | 17 | 14 |
| 150 | 18 | 17 | 34 | 18 | 22 |
| 100 | 149 | 150 | 121 | 171 | 134 |
| 100 | 167 | 200 | 138 | 178 | 150 |
| 75 | 400 | 325 | 350 | 350 | 300 |
| 75 | 344 | 300 | 375 | 350 | 350 |
| Average Test Results | | | | | |
| 150 | 17 | 17 | 30 | 18 | 18 |
| 100 | 158 | 175 | 130 | 175 | 142 |
| 75 | 372 | 313 | 363 | 350 | 325 |

The soluble cutting oils of the invention resist microbial degradation and do not contain biocides. In drill-life tests, they performed as well as industry standards. Bioresistance is achieved by selecting surfactant molecules which contain branches in the carbon skeleton. To enhance this bioresistance, basestocks may be selected which also contain branches, such as multiple methyl groups. Further, enhanced performance is obtained by using phosphorous and boron containing additives. Overall, the most preferred cutting oil used polypropene as basestock and isohexadecanoic acid, in soap form, as primary surfactant.

What is claimed is:

1. A stable cutting oil emulsion comprising a bioresistant cutting fluid composition and water in a volume ratio of the bioresistant cutting fluid composition to the water of between 0.5:100 to 10:100; the bioresistant cutting fluid composition comprising
   (a) a soap derived from a carboxylic acid compound selected from the group consisting of isohexadecanoic acid and isoeicosanoic acid, having the formula:

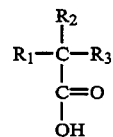

wherein $R_1$ is a hydrogen atom or an alkyl group; $R_2$ is a hydrogen atom or an alkyl group and $R_3$ is an alkyl group, the number of carbon atoms of $R_1$ plus $R_2$ plus $R_3$ being either 14 or 18, provided that when $R_1$ and $R_2$ are hydrogen, the $R_3$ alkyl group has a branched carbon skeleton, wherein the soap is formed in situ from the amine, an alkali metal or (d); and (b) a lubricative basestock material which comprises a hydrocarbon component having a branched carbon skeleton, the branching being sufficient to provide bioresistance to the basestock material, the hydrocarbon component is selected from the group consisting of a polypropene which contains a methyl group on every second carbon atom in the backbone; copolymers of propylene and butene; polybutene; polyisobutylene; and liquid ethylene-propylene copolymer;
   (c) an alcohol ethoxyphosphate;
   (d) a triethanolamine;
   (e) a boric acid ester of an alkanolamine selected from the group consisting of boric acid esters of mono- and tri-ethanolamine; and
   (f) 2,4,7,9-tetramethyl-5-decyne-4,7-diol.

2. The bioresistant cutting fluid emulsion of claim 1 in which the carboxylic acid is isohexadecanoic acid.

3. The bioresistant cutting fluid emulsion of claim 1 in which the carboxylic acid is isoeicosanoic acid.

4. The bioresistant cutting fluid emulsion of claim 1 in which the lubricative basestock is polypropene which contains a methyl group on every second carbon atom in the backbone.

5. The bioresistant cutting fluid emulsion of claim 1 in which the lubricative basestock is a copolymer of propylene and butene.

6. The bioresistant cutting fluid emulsion of claim 1 in which the lubricative basestock is polybutene.

7. The bioresistant cutting fluid emulsion of claim 1 in which the lubricative basestock is polyisobutylene.

8. The bioresistant cutting fluid emulsion of claim 1 in which the lubricative basestock is liquid ethylene-propylene copolymer.

* * * * *

UNITED STATES PATENT AND TRADEMARK OFFICE
CERTIFICATE OF CORRECTION

PATENT NO. : 5,417,869
DATED : May 23, 1995
INVENTOR(S) : T. J. Giacobbe et al.

It is certified that error appears in the above-indentified patent and that said Letters Patent is hereby corrected as shown below:

In claim 1, Col. 14, line 17, after "amine" delete ", an alkali metal or"

Signed and Sealed this

Twelfth Day of September, 1995

Attest:

BRUCE LEHMAN

Attesting Officer

Commissioner of Patents and Trademarks